United States Patent
MacAdam et al.

(10) Patent No.: US 6,944,495 B2
(45) Date of Patent: Sep. 13, 2005

(54) METHODS FOR PROCESSING ELECTROCARDIAC SIGNALS HAVING SUPERIMPOSED COMPLEXES

(75) Inventors: David P. MacAdam, Millbury, MA (US); Paul J. Wang, Saratoga, CA (US); Shawn Yang, Andover, MA (US); Dipen Shah, Talence (FR)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/618,441

(22) Filed: Jul. 11, 2003

(65) Prior Publication Data

US 2004/0127805 A1 Jul. 1, 2004

Related U.S. Application Data

(63) Continuation-in-part of application No. 10/005,470, filed on Nov. 7, 2001.
(60) Provisional application No. 60/247,269, filed on Nov. 10, 2000, and provisional application No. 60/295,217, filed on Jun. 1, 2001.

(51) Int. Cl.$^7$ .................................................. A61B 5/04
(52) U.S. Cl. ......................................................... 600/521
(58) Field of Search ................................. 600/508–525

(56) References Cited

U.S. PATENT DOCUMENTS

| | | | |
|---|---|---|---|
| 4,336,810 A | 6/1982 | Anderson et al. | |
| 4,721,114 A | 1/1988 | DuFault et al. | |
| 4,793,361 A | 12/1988 | DuFault | |
| 5,311,873 A | 5/1994 | Savard et al. | |
| 5,609,157 A | 3/1997 | Panescu et al. | |
| 5,713,367 A | 2/1998 | Arnold et al. | |
| 5,758,654 A | 6/1998 | Burton-Krahn et al. | |
| 5,772,604 A | 6/1998 | Langberg et al. | |
| 5,778,881 A | 7/1998 | Sun et al. | |
| 5,827,195 A | 10/1998 | Lander | |
| 5,840,038 A | 11/1998 | Xue et al. | |
| 6,035,231 A | 3/2000 | Sornmo et al. | |
| 6,230,048 B1 | 5/2001 | Selvester et al. | |
| 6,490,479 B2 | 12/2002 | Bock | |
| 6,491,629 B1 | 12/2002 | Bousseljot et al. | |
| 6,615,075 B2 * | 9/2003 | Mlynash et al. | 600/513 |
| 2001/0056245 A1 | 12/2001 | Mlynash et al. | |
| 2001/0056289 A1 | 12/2001 | Groenewegen | |

FOREIGN PATENT DOCUMENTS

| | | |
|---|---|---|
| EP | 0 848 965 A2 | 6/1998 |
| WO | WO-91/02484 A1 | 3/1991 |
| WO | WO-98/09241 A1 | 3/1998 |
| WO | WO-01/67950 A1 | 9/2001 |
| WO | WO-01/67954 A1 | 9/2001 |
| WO | WO-01/76461 A2 | 10/2001 |
| WO | WO-02/058550 A2 | 8/2002 |
| WO | WO-03/022148 A1 | 3/2003 |

OTHER PUBLICATIONS

P.W. Hsia et al., "Computer Arrhythmia Analysis in an Excercise System," Proc.Ann. Conf. on Eng. in Medicine and Biology, 65 (1985).

R.D. Throne et al., "Use of Tachycardia Templates for Recognition of Recurrent Monomorphic Ventricular Tachycardia," Proc. Computers in Cardiology Meeting, 171–174 (1989).

S.E. Greenhut et al., "Template Matching Techniques for Electrophysiologic Signals: A Practical, Real–Time System for Detection of Ventricular Tachycardia," Biomedical Sciences Instrumentation, 37–42 (1992).

(Continued)

Primary Examiner—George Manuel
(74) Attorney, Agent, or Firm—Darby & Darby

(57) ABSTRACT

Computer implemented methods and associated systems are disclosed for processing electrical signals recorded from the heart and, more particularly, for objectively deriving subcomponents and comparing signals and their subcomponents.

30 Claims, 10 Drawing Sheets

OTHER PUBLICATIONS

G.F. Michaud et al., "Correlation Waveform Analysis to Discriminate Monomorphic Ventricular Tachycardia from Sinus Rhythm Using Stored Electrograms from Implantable Defibrillators," PACE 22(8): 1146–1147 (1999).

International Search Report dated Nov. 21, 2002 for International patent application No. PCT/US01/46348.

Shelly A. Stevenson, et al., "Analysis of the Intraventricular for Differentiation of Distinct Monomorphic Ventricular Arrhythmias", PACE—Pacing and Clinical Electrophysiology, Nov. 1997, vol. 20, No. 11, pp. 2730–2738.

John P. Marenco, et al., "Testing of a New T–Wave Substraction Algorithm as an Aid to Localizing Ectopic Atrial Beats", A.N.E., Jan. 2003, vol. 8, No. 1, pp. 55–59.

* cited by examiner

METHODS FOR PROCESSING ELECTROCARDIAC SIGNALS HAVING SUPERIMPOSED COMPLEXES

This patent application is a continuation of U.S. patent application Ser. No. 10/005,470, filed Nov. 7, 2001, entitled Methods for Processing Electrocardiac Signals Having Superimposed Complexes, which claims the benefit of priority under 35 U.S.C. § 119 of U.S. Provisional Application Serial No. 60/247,269, filed Nov. 10, 2000, entitled "Method for Viewing and Comparing ECG Signals Having Superimposed Complexes," and U.S. Provisional Application Serial No. 60/295,217, filed Jun. 1, 2001, entitled "An Algorithm to Measure T-wave Subtraction Quality," the entirety of these applications being hereby incorporated by reference.

FIELD OF THE INVENTION

This invention relates to a method for processing electrical signals obtained from the heart and, more particularly, to a method for processing electrocardiac signals having superimposed sub-component complexes to enable tracking of native, paced, and derived beat signals.

BACKGROUND OF THE INVENTION

Certain cardiac arrhythmias are triggered or initiated from a site in the heart tissue other than the sinus node. These arrhythmias are generally classified as being "focal" in nature. Treatment of focal arrhythmias generally involves locating the arrhythmogenic site and ablating it. One method for regionally locating the focal site is the use of a diagnostic 12 Lead ECG. The 12 Lead can be used in conjunction with pacing via a roving intracardiac catheter to pace map the heart. The theoretical basis of this method assumes that the paced 12 lead ECG will appear identical to the non-paced ECG if the cycle length (i.e., paced heart rate) and pacing site matches the non-paced heart rate and focal site of origin.

One problem with this method (in current practice) is the subjectivity involved in visually comparing a non-paced 12 Lead ECG to a paced 12 Lead ECG.

A second problem is the time consuming nature of the procedure in which, typically, a spontaneous ectopic beat is recorded and printed on paper. A roving mapping catheter is positioned at a likely site of ectopy, pacing is initiated, a recording is made, a printout is generated and a visual comparison is made by aligning the printouts from the spontaneous and paced beats over one another. This process is repeated in an iterative manner until the physician determines that a good match between the spontaneous ectopic beat and the paced beat is found.

A third problem arises when multiple arrhythmogenic foci are present and each focus produces a variant on the 12 Lead ECG. Better discrimination between these foci would be advantageous during pace mapping as well as during other EP procedures. (Ref.—Throne R D, Jenkins J M, Winston S A, et al. "Use of tachycardia templates for recognition of recurrent monomorphic VT." Comp. Cardiology 1989:171–174.)

A fourth problem involves the superimposition of the P-wave and T-wave components of the ECG. The electrocardiogram typically includes an initial impulse, termed the P-wave, emanating from the atria, followed by what is termed the QRS complex, emanating from the ventricles, which is followed by a T-wave resulting from repolarization of the ventricles (FIG. 1). Thus, a heart beat begins with the P-wave and ends with the T-wave, and the next heart beat begins with another P-wave.

The P-wave can be a valuable tool used by clinicians to diagnose the condition of the heart. Thus, clinicians will often monitor an electrocardiogram (ECG) of the heart to aid in the diagnosis of atrial and ventricular arrhythmias. This can be done in various ways, such as by monitoring the 12 Lead (surface) ECG in conjunction with observing the bioelectric activity recorded on intracardiac electrodes carried by a transthoracic catheter.

In some focal arrhythmias the atrial heart tissue begins to beat very rapidly as the focal origin moves from the sinus node to an ectopic site. Sometimes this higher heart rate is sustained over three or more beats and is termed a tachycardia. Other times the higher rate is intermittent and may be as short as one heart beat. In either case, the first beat of the atrial arrhythmia is usually initiated by what is termed a Premature Atrial Contraction ("PAC") which can result in the P-wave of a successive heart beat overlapping with the T-wave of the preceding beat (FIG. 2). Not only is this a physiologically compromised state for the heart to be in, but the clinician can no longer use the P-wave to diagnose the heart because it is obscured by the T-wave.

Accordingly, it will be apparent that there continues to be a need for a method that allows a clinician to Pace Map more effectively and in addition monitor the P-wave of a patient's heart beat, even when the P-wave is overlapping with a preceding T-wave. The instant invention addresses these needs.

And while T-wave subtraction is a useful method in electrophysiology procedures to unmask the ECG P-wave morphology of a PAC by subtracting a QRS-T template from a PAC, ECG baseline drift caused by respiration or body movement may cause certain variations on the results of T-wave subtraction. Thus, a further need remains in the art to quantitatively measure the quality of T-wave subtraction results, among other reasons to monitor the respiration variations on T-wave subtraction. The instant invention addresses this need as well.

SUMMARY AND OBJECTS OF THE INVENTION

The present invention, in certain aspects, provides a medical practitioner with a computerized method for objectively and efficiently performing real time pace mapping and other cardiac analyses, through the processing of incoming electrical signals which represent heart activity to display a derived P-wave without any overlap with a preceding T-wave during a PAC, and to allow the practitioner to objectively compare derived P-waves to determine if they are emanating from the same focus. As a direct consequence of the cardiac signal processing of the present invention, otherwise masked signals and correlations are identified among heart beats and segments of heart beats through calculations on acquired signals and/or derivations of new signals. The practitioner can be guided through visual aids such as bar graphs and overlaid cardiac signals of the quality of signal matches. These signal matches can assist in diagnosing a patient and in the effectiveness of an ongoing treatment, for example, an ablation procedure.

Due to timing and amplitude relationships among beats of a heart, there is the possibility that individual waveforms can be obscured or hidden. If a singular, unadulterated sub-component waveform is identified, and if this sub-component has similar timing characteristics that allow it to be synchronized with the composite waveform, then a subtraction process can be performed in accordance with an aspect of the invention to thereby derive the other subcomponent waveform(s). Sub-component waveforms, either derived, native state, or pace induced, can be quantitatively compared to one another using correlation analysis. This analysis may be done retrospectively or in real time.

More specifically, the present invention provides systems, programmed machines, and methods that permit superior signal processing over prior art electrophysiology signal processors and can achieve this using a standard 12 lead ECG.

In accordance with one aspect of the invention, a system for tracking ectopic beats comprises a signal sensing unit, a signal processor, and an output device. The signal sensing unit is configured to capture a first ECG signal. The signal processor is connected to receive the first ECG signal from the signal sensing unit and is configured to permit a user to mark a begin point and an end point of the first ECG signal for use in defining a waveform segment as a reference template, to acquire data from multiple leads, and to identify a best fit between the reference template and the acquired data using a correlation coefficient calculation. The output device presents the identified best fit.

In accordance with another aspect of the invention, a system for deriving a p-wave signal from a premature atrial contraction ("PAC") beat comprises a signal sensing unit, a signal processor, and an output device. The signal processor is connected so as to receive electrocardiac signals from the signal sensing unit and is configured to process the electrocardiac signals so as to derive the P-wave signal from the PAC beat. The output device presents the derived P-wave signal.

In a particular embodiment of the foregoing system, the processor is configured to execute the steps of: (a) selecting a QRS-T segment of a reference ECG signal; (b) permitting a user to mark a begin point and an end point of the selected ECG signal; (c) defining a reference template as being a waveform segment between the marked begin and end points of the selected ECG signal; (d) acquiring the PAC beat at the signal processing unit from multiple leads (preferably with no more than 12 leads); and (e) processing the PAC beat so as to derive the P-wave signal.

In accordance with still another aspect of the invention an electrophysiology computer system includes a processor that is configured to derive a P-wave signal hidden within a premature atrial contraction ("PAC") beat. The processor executes the steps of: (a) selecting a QRS-T segment of a reference ECG signal; (b) permitting a user to mark a begin point and an end point of the selected segment of the reference ECG signal; (c) defining a reference template as being a waveform segment between the marked begin and end points of the selected segment of the reference ECG signal; (d) acquiring the PAC beat at the signal processing unit from multiple ECG leads; and (e) processing the PAC beat so as to derive the p-wave signal.

In a particular embodiment of the foregoing system, the processor utilizes a correlation coefficient calculation to effect a subtraction of the reference template from a predetermined segment of the PAC beat. In more particular embodiments, the processor is configured to compare derived P-waves from multiple beats to one another, to indicate or infer a common focal origin among several derived P-waves, to predict the most likely site of the origin of a focus using a (preferably 12 lead) library of p-waves of known focal origin, to derive paced P-waves for comparison to spontaneous p-waves, to determine an integral value of the QRS area of a derived P-wave signal, to normalize any integral values over a length of the derived P-wave signal, to process the QRS segment of a beat separately to arrive at further determinations concerning the heart beat data, and to perform combinations of the foregoing.

In accordance with still another aspect of the invention an electrophysiology computer system includes a processor that is configured to execute steps substantially in the same manner as the processor that derives a P-wave from a PAC beat, but more generally is configured to derive a non-synchronous subcomponent from a first heartbeat signal having a composite waveform which includes a synchronous subcomponent overlapping the non-synchronous subcomponent. The processor executes the steps of selecting a synchronous subcomponent of a second heartbeat signal which corresponds to the synchronous subcomponent of the first heartbeat signal; permitting a user to mark a begin point and an end point of the selected synchronous subcomponent; defining a reference template as being a waveform segment between the marked begin and end points of the selected synchronous subcomponent; acquiring the composite waveform of the first heartbeat signal at the signal processing unit from multiple leads; and processing the composite waveform beat so as to derive the non-synchronous subcomponent.

In accordance with yet further aspects of the invention, a method for tracking ectopic beats through template matching is described which includes the steps of: (a) capturing a first ECG signal in a signal processing unit; (b) permitting a user to mark a begin point and an end point of the captured first ECG signal; (c) defining a reference template as being a waveform segment between the marked begin and end points of the first ECG signal; (d) acquiring data at the signal processing unit; and (e) using a correlation coefficient calculation on the acquired data to identify a best fit between the reference template and the acquired data.

In accordance with further aspects of the invention, a method for deriving a P-wave signal from a premature atrial contraction ("PAC") beat is described which can assist a person in diagnosing a heart. This method includes the steps of: (a) selecting a QRS-T segment of a reference ECG signal; (b) permitting a user to mark a begin point and an end point of the selected segment of the reference ECG signal; (c) defining a reference template as being a waveform segment between the marked begin and end points of the selected segment of the reference ECG signal; (d) acquiring the PAC beat at the signal processing unit from multiple leads; and (e) processing the PAC beat so as to derive the p-wave signal.

In a particular embodiment of the foregoing methods, the PAC beat is processed using a correlation coefficient calculation to effect a subtraction of the reference template from a predetermined segment of the PAC beat. Also, the foregoing methods can include the additional steps of: comparing derived p-waves from multiple beats to one another; indicating or inferring a common focal origin among several derived p-waves; predicting the most likely site of the origin of a focus using a (preferably 12 lead) library of P-waves of known focal origin; deriving paced P-waves for comparison to spontaneous P-waves; determining an integral value of the QRS area of a derived P-wave signal; normalizing any integral values over a length of the derived p-wave signal; processing QRS segment of a beat separately to arrive at further determinations concerning the heart beat data, and performing combinations of the foregoing steps.

Further methods according to still further aspects of the invention include the determination of integrals concerning a section of the QRS-T segment and the processing of those integrals. A QRS segment integral can be used as a measure of the QRS residue, which is an indicator of the alignment or synchronization quality between the template QRS and the PAC QRS Furthermore, baseline drift can be monitored as a change of the QRS absolute peak (integral) value percentage between the template and the PAC. These methods are implemented by suitably configured computer processors.

Yet a further method in accordance with another aspect of the invention proceeds in substantially the same manner as when deriving a p-wave from a PAC beat, but more generally includes the selecting the synchronous subcomponent of the heartbeat signal, permitting a user to mark a begin point and an end point of the selected synchronous subcomponent, defining a reference template as being a waveform segment between the marked begin and end points of the selected synchronous subcomponent, acquiring the composite waveform at the signal processing unit from multiple leads, and processing the composite waveform beat so as to derive the non-synchronous subcomponent.

In accordance with the invention, a compare display method for displaying sequential paced signal/template matches is provided that decreases the time required to perform a pace-mapping procedure. In one embodiment, the compare display method includes the steps of simultaneously displaying a template, a most recent paced signal/template match, and a second-most recent paced signal/template match. In another embodiment, the compare display method includes the steps of simultaneously displaying a template, a most recent paced signal/template match, and a previous paced signal/template best match.

In accordance with a further aspect of the present invention, a template optimization method is disclosed which dynamically employs different templates. QRS beats that precede or follow a PAC can be selected manually or by action of a programmed machine in selecting and setting a new template for use in subsequent calculations. The method is implemented by suitably configured computer processors.

Other aspects, features and advantages of the invention can be more clearly understood from the following detailed description of exemplary embodiments and accompanying Drawing Figures.

DESCRIPTION OF THE DRAWING FIGURES

FIGS. 10 (a), (b) and (c) is a schematic diagram of real-time template matching without (a) and with (b), (c) a trigger and offset.

Figure 11:
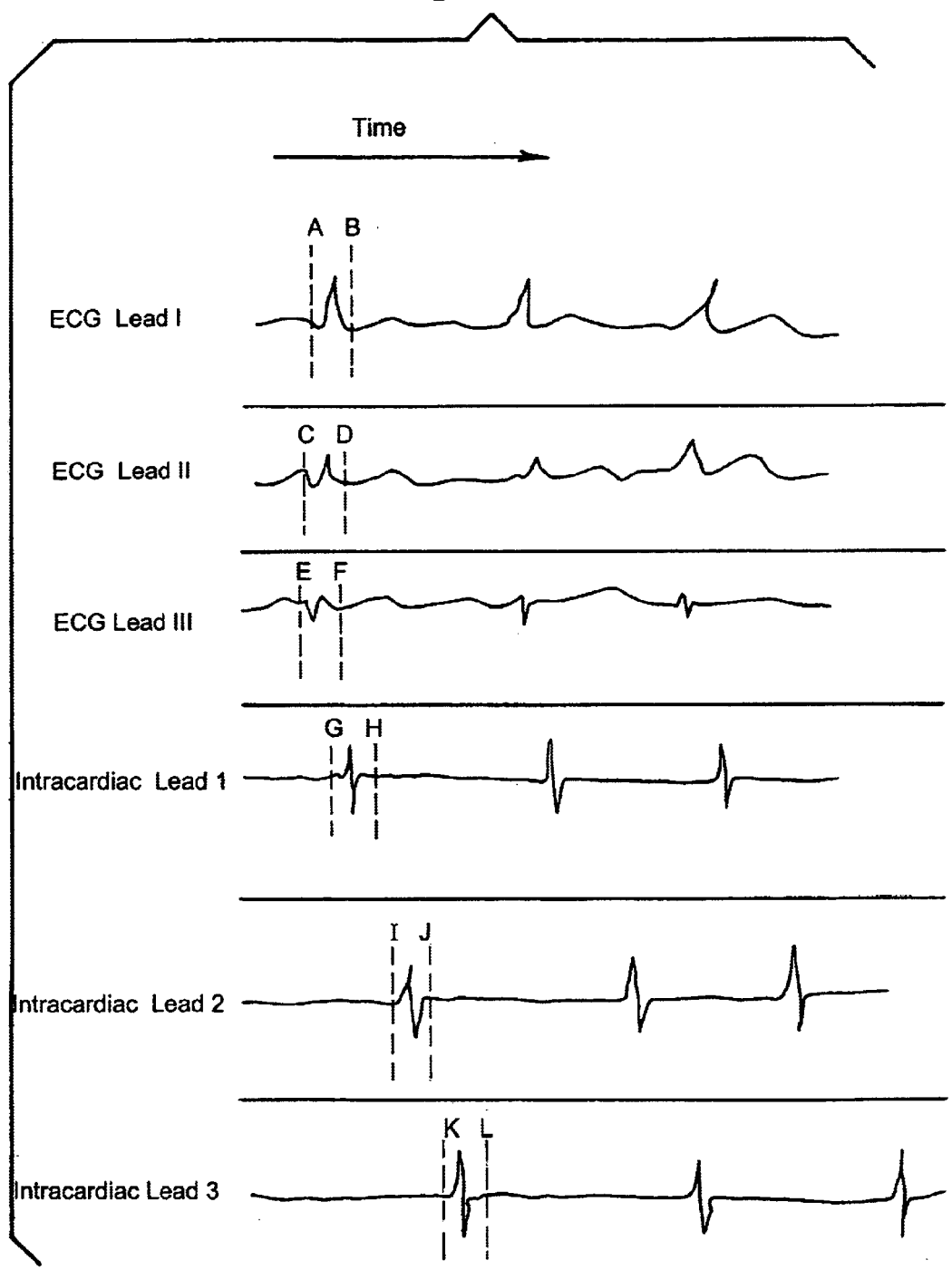

FIG. 11 is a schematic diagram of a template constructed of signals selected from multiple leads at varying times.

DETAILED DESCRIPTION OF THE PREFERRED EMBODIMENTS

To promote an understanding of the methods that can be practiced in accordance with preferred embodiments of the present invention, several pertinent aspects are discussed below under respective headings.

Template Matching/Pace Mapping

Any recorded ECG waveform can be used as a reference to compare to another recorded ECG waveform or to a real time ECG waveform. The comparison is performed in a two step process in which first a reference template is selected by the user to describe the beginning and end of an ECG waveform segment to be used as a comparison template. Next the user selects the region of data to be used for comparison—either from pre-recorded data or from the real time data stream. A suitably configured computer processor can find the best match against the reference template over the region specified, or in the case of real time analysis, find the best match updated over a defined period of time, for example every second. The criteria for "best match" utilizes a correlation coefficient calculation across all twelve leads of the ECG and finds the best alignment. This calculation may be preceded by a correlation assessment that is taken across fewer leads, such as only one lead, to generally align the reference template to the selected region of data that is of interest. A visual display showing the aligned reference beat (template) overlaid on the beat undergoing analysis give the user feedback as to the closeness of the match. A correlation coefficient calculated for each ECG lead gives a quantitative indicator of the match. A composite average is also calculated and is displayed in a unique color enhanced bar graph indicator which is especially useful when real time template matching is being performed. The composite average can be updated as a moving average over a preselected number of beats.

Template matching may be used to compare two spontaneous beats or it can be used to pace map, i.e., to compare a paced beat to a spontaneous beat. A Region of Interest (ROI) indictor can be manipulated by the user to exclude certain portions of the waveform from analysis. This is useful during pace mapping where pacing artifacts on the surface leads can be excluded from the region of analysis. The ROI indicator can also be used to specify a preference for T-wave or P-wave matching as they are oftentimes morphologically very similar.

T-Wave Subtraction

In one embodiment of the present invention, a method is provided whereby an ECG having an overlapping P and T wave is processed to remove the T-wave and thereby display the P-wave without any overlap, so that a clinician may observe the P-wave when performing a diagnosis of the heart.

Figure 1:
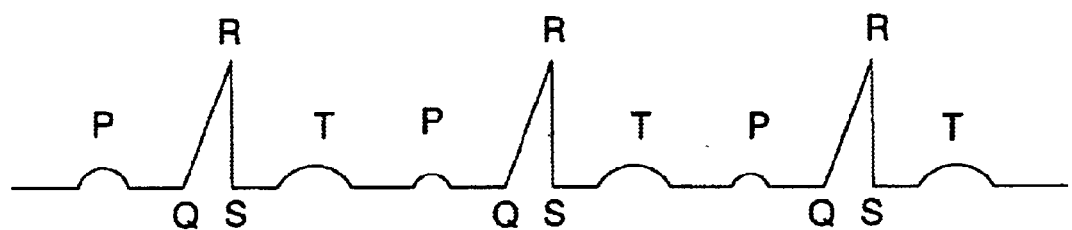
FIG. 1 is a schematic diagram of a normal heart beat.
Figure 2:
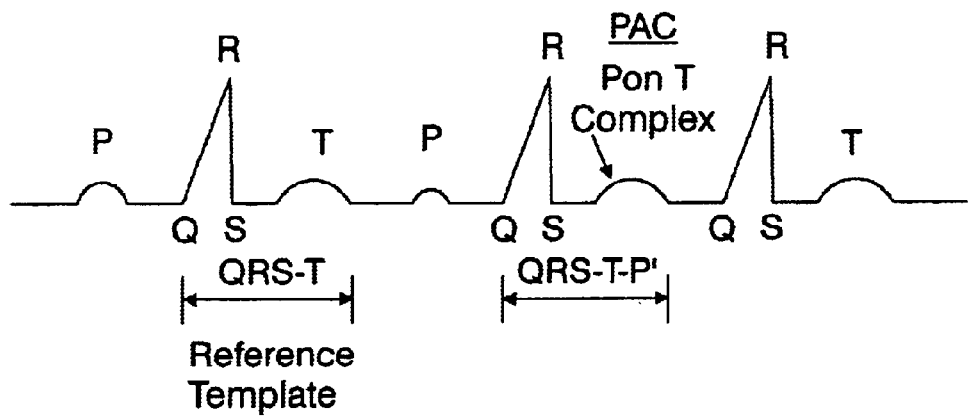
FIG. 2 is a schematic diagram of a pre-mature atrial contraction (PAC)

See FIG. 1 which describes a normal ECG over three beats in which distinctive P and T-waves can be identified. FIG. 2 shows a rhythm in which the P-wave from the third beat (P') arrives early and is obscured by the T-wave from the second beat. This results in what is termed a P on T complex, and is referred to as a QRS-T-P' in the figure.

In general, according to the method, the QRS-T segment of a beat that lacks a PAC is selected as a template. This template is subtracted from the QRS-T-P' signal in the PAC to be studied yielding the P-wave. The QRS-T signal used as the template may be from a single beat or it may be derived from an average of multiple beats. The QRS-T signal (or average) used as the template is selected so that the preceding QRS-QRS interval is equal (or nearly equal) to the QRS-QRS interval immediately preceding the QRS-T-P' signal to be studied. Preferably, the beat immediately preceding the PAC can be used for the selected QRS-T template as the cycle length and hemodynamic conditions of this beat are the closest to those of the succeeding beat that contains the PAC and P on T complex. (See FIGS. 2 and 3.)

The QRS complex is used as a means to synchronize and align the QRS-T template and the PAC beat for subtraction. The alignment is automated by the algorithm for the best match based on the composite correlation coefficient across the 12 Lead ECG. The practitioner has the option of shifting the template match left or right on a sample by sample basis with the resulting composite correlation coefficient updated at each new position. The practitioner also has the option of choosing the previous or following QRS-T segment as the reference template. The software will automatically locate the previous or following beat based on the current reference template and use the corresponding QRS-T segment of that beat as the new reference template in the calculation of derived P-waves.

Different display views showing the derived P-wave, alone, or overlaid with the original PAC beat or reference template are available as an aid to the practitioner.

P-waves that have been derived using the T-wave subtraction method can be signal processed further to remove unwanted artifacts caused by respiration or noise.

3. Template Matching of Derived P-Waves

Once one has a derived P-wave identified from the tachycardia or premature atrial beat (PAC), one can compare this derived P-wave with a previously captured reference template.

3a. More specifically, one or more spontaneous P-waves may be identified using the subtraction method described above and compared with one another using a correlation waveform analysis. This can be used to determine if the spontaneous P-waves have the same focal origin. This can be done in real time or in review from recorded data.

3b. In addition, one or more derived spontaneous P-waves may be identified and compared to a library of P-waves of known focal origin to predict the most likely site of origin.

3c. In addition, once a derived spontaneous P-wave is identified by the T-wave Subtraction method as described above then the practitioner can begin atrial pace mapping following the Template Matching/Pace Mapping method also described above. The roving pace mapping catheter is maneuvered within the atria (or adjacent vessels such as the pulmonary veins) until the derived paced P-wave is nearly identical to the derived spontaneous P-wave. This comparison of derived P-waves may be done on pre-recorded data or in real time.

More generally, two or more waveforms X, Y, ..., may form a composite waveform that due to timing and amplitude relationships causes the individual waveforms to be obscured or hidden. The composite waveform includes a synchronous subcomponent overlapping a non-synchronous subcomponent. If a singular, unadulterated sub-component waveform (e.g. X or Y) can be identified, and if it has similar timing characteristics that allow it to be synchronized with the composite waveform (i.e., this identified subcomponent is the synchronous subcomponent), then it can be subtracted from the composite waveform to derive the other sub-component waveform(s) (i.e., the non-synchronous subcomponent(s)). Sub-component waveforms, either derived, native state, or pace induced, can be quantitatively compared to one another using correlation analysis. This analysis may be done retrospectively or in real time. One of skill in the art will appreciate that a number of algorithms can be used to compare waveform shape, including, but not limited to bin area methods and integrals; any of these methods can assist in the goals of aligning synchronous components of composite waveforms and/or comparing the derived results.

A method in accordance with this more general teaching proceeds generally as outlined above. Specifically, this method proceeds in substantially the same manner as when deriving a P-wave from a PAC beat, but more generally includes the selecting the synchronous subcomponent of the heartbeat signal, permitting a user to mark a begin point and an end point of the selected synchronous subcomponent, defining a reference template as being a waveform segment between the marked begin and end points of the selected synchronous subcomponent, acquiring the composite waveform at the signal processing unit from multiple leads, and processing the composite waveform beat so as to derive the non-synchronous subcomponent.

Figure 4:
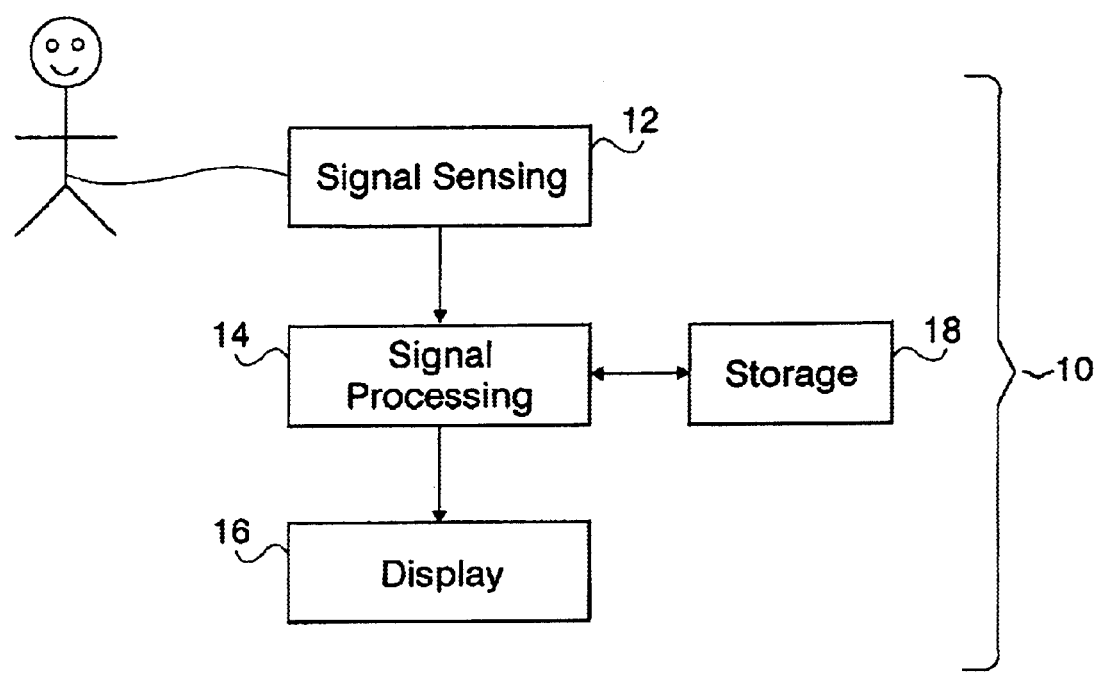
FIG. 4 is a block diagram of a system programmed to practice a method in accordance with a preferred embodiment of the present invention.

Referring now to the drawings, and particularly to FIG. 4, there is shown a system 10 for receiving and processing electrical signals according to one illustrative embodiment of the present invention. In one illustrative embodiment, the system 10 includes a signal sensing unit 12, which may take different forms, such as a standard 12 lead ECG, intracardiac lead, or combination thereof. The signal sensing unit is electrically connected to a signal processing device 14, which receives the sensed signals from the unit 12 and processes the signals, as is described in more detail below. The signal processing device ("signal processor" or "processor") 14 is preferably connected to a suitable display 16, which will present the processed signals to a clinician or other interested person. Information can be stored and recalled from a storage device 18. Preferably the signal processing device 14 and display 16 comprise the EP LabSystem (trademark) of C.R. Bard, Inc., Murray Hill, N.J., or the like. The EP LabSystem (trademark) supports a variety of data gathering and processing functions that are standard in electrophysiology procedures, and can have its hardware (namely, processor 14) configured to implement the subtraction and derivation methods set forth above, for example, through software (e.g., modules, procedures, functions, or objects) or firmware. The processor 14 communicates with a memory or storage 18 which configures the processor to implement the subtraction and derivation methods above (as well as the integral techniques described below).

In one illustrative embodiment, the special features of the system of the present invention are implemented, in part, by a processor using program information stored in a memory of the signal processing device 14. The processor 14 can access one or more files, as necessary, to implement the required functions, as described in greater detail in connection with FIG. 5 and FIG. 6.

Figure 5:
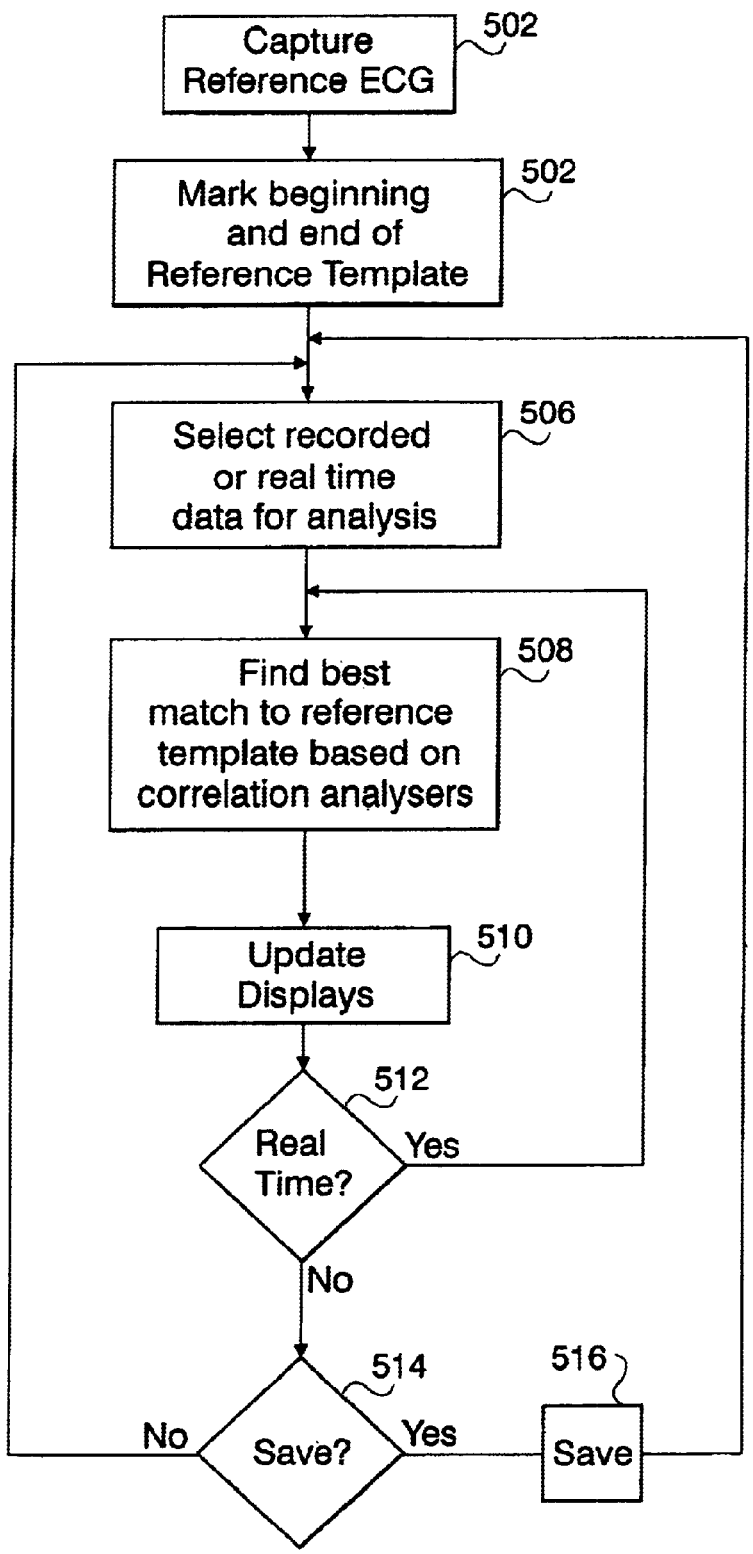
FIG. 5 is a flow diagram showing the process for template matching in accordance with the preferred embodiment.

Referring now to FIG. 5, the operation of the signal processing device 14 of the present invention is described in conjunction with the above structural description of the system 10. As illustrated in FIG. 5, the process begins when a clinician desires to create a reference template, and this occurs by capturing a reference ECG signal, as indicated at step 502. Preferably, the reference ECG signal is captured using a standard 12 lead device and/or one or more intracardiac leads. As explained above in connection with FIG. 2, the QRS-T signal components of a beat which does not exhibit P- on T-wave are selected as a template and it is this set of electrocardiac signal components that is captured at step 502. Such a beat can be captured in sinus rhythm or during a focal arrhythmia such as a tachycardia. Furthermore, it is contemplated that the reference template results from signals captured either at the surface, from intracardiac leads that can be placed in a variety of locations within the heart, or a combination of signals from surface and intracardiac leads. The QRS-T signal that is used as the template can be captured from a single heartbeat or may be a signal derived from an average of multiple heart beats.

At step 504, beginning and end points of the reference template are marked by the clinician using an interface to the signal processing unit 14. The marked points define the segment of the ECG waveform to be used as a comparison template.

At step 506, the clinician selects whether recorded or real-time data is to be used in the template matching analysis. (This step can be performed at any time prior to the waveform matching analysis at step 508, for example, prior to performing steps 502 and 504.) If recorded data is to be used in the template matching analysis, then a specified region of pre-recorded data is provided to the signal processing unit for comparison to the reference template. On the other hand, if real-time data is to be used in the template matching analysis, a stream of data from ECG leads is provided to the signal processing unit 14 over a defined period of time for comparison to the reference template.

At step 508, the signal processor 14 finds a "best match," in other words, a best alignment between the selected region or time period and the reference template.

At step 510, the display 16 is updated to indicate to the clinician (or other persons) the result of the template match. The results can be shown qualitatively as superimposed ECG waveform signals, namely, the reference beat (template) overlaid upon the beat under analysis to show the degree of alignment therebetween, or quantitatively as a correlation coefficient calculated for each ECG lead. Preferably, a composite average is also calculated and displayed. This is illustrated in the computer display shown in FIG. 8.

Figure 8:
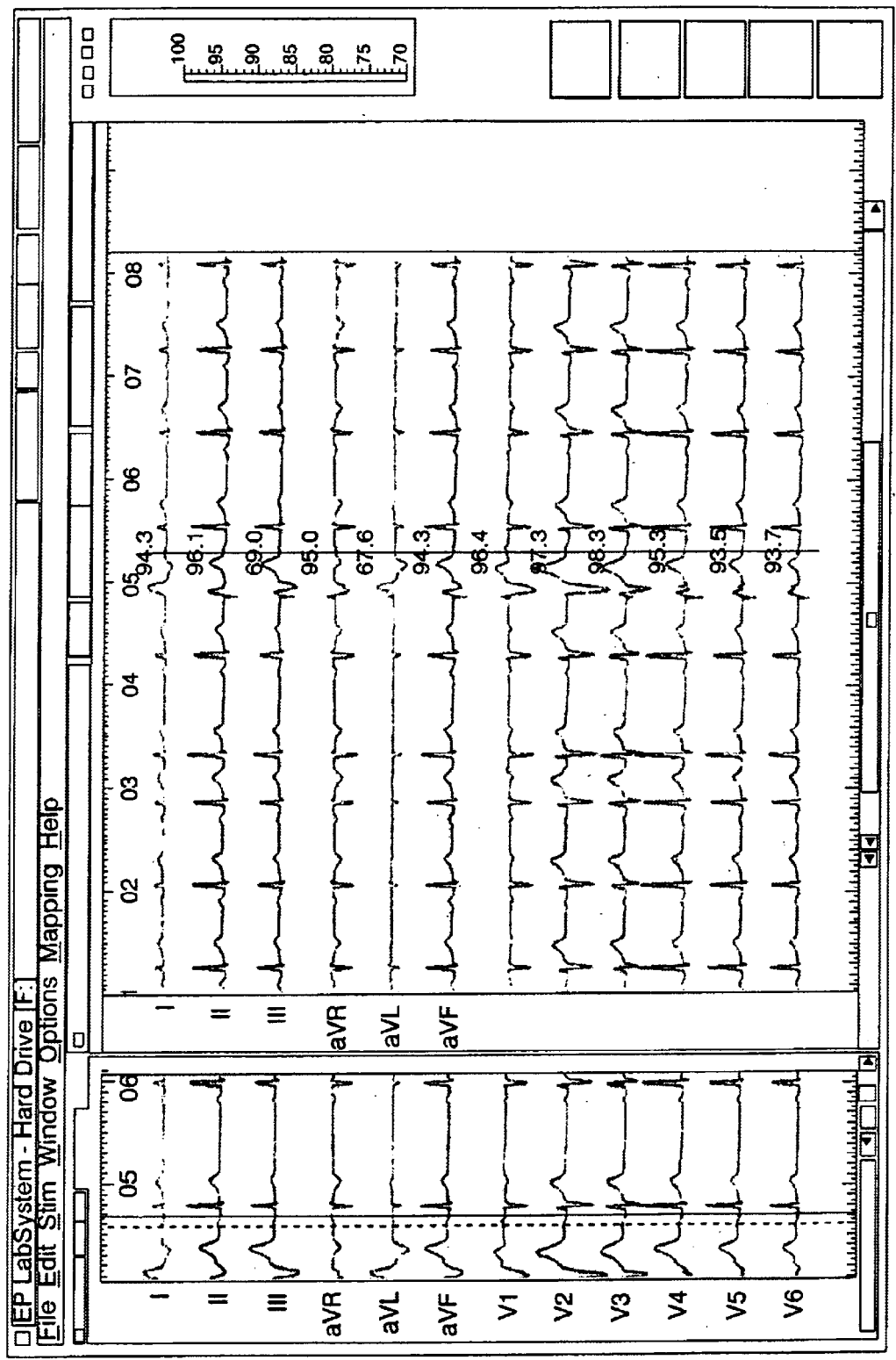
FIG. 8 is a representative computer display interface for template matching that can be displayed to an operator.
Figure 8A:
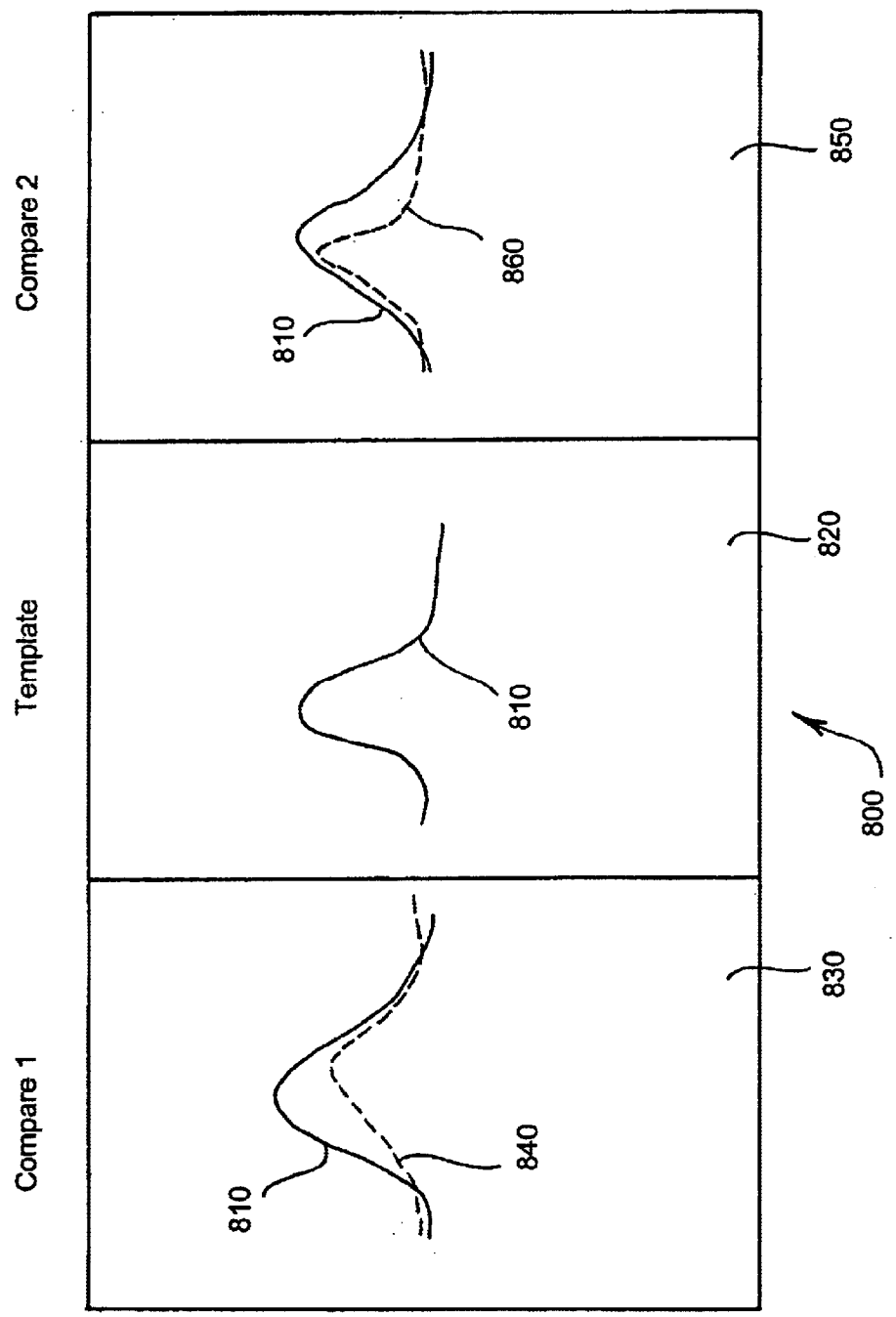
FIG. 8A is a schematic diagram of a multi-signal display of waveform correlations to a template.

FIG. 8(a) illustrates a compare display in which the second-most recent paced signal/template match (compare 1), the template, and the most recent paced signal/template match (compare 2) are simultaneously displayed.

At step 512, a test is made to determine whether the user had selected real-time processing at step 506. If so, then the flow loops back to step 508 to again perform the template matching analysis and to update the display accordingly. Otherwise, if previously recorded segments are being analyzed, the user is given the option to save the analysis (as tested at step 514), and the correlation analysis is saved, as indicated at step 516. Real-time analyses can also be saved if desired.

Figure 6:
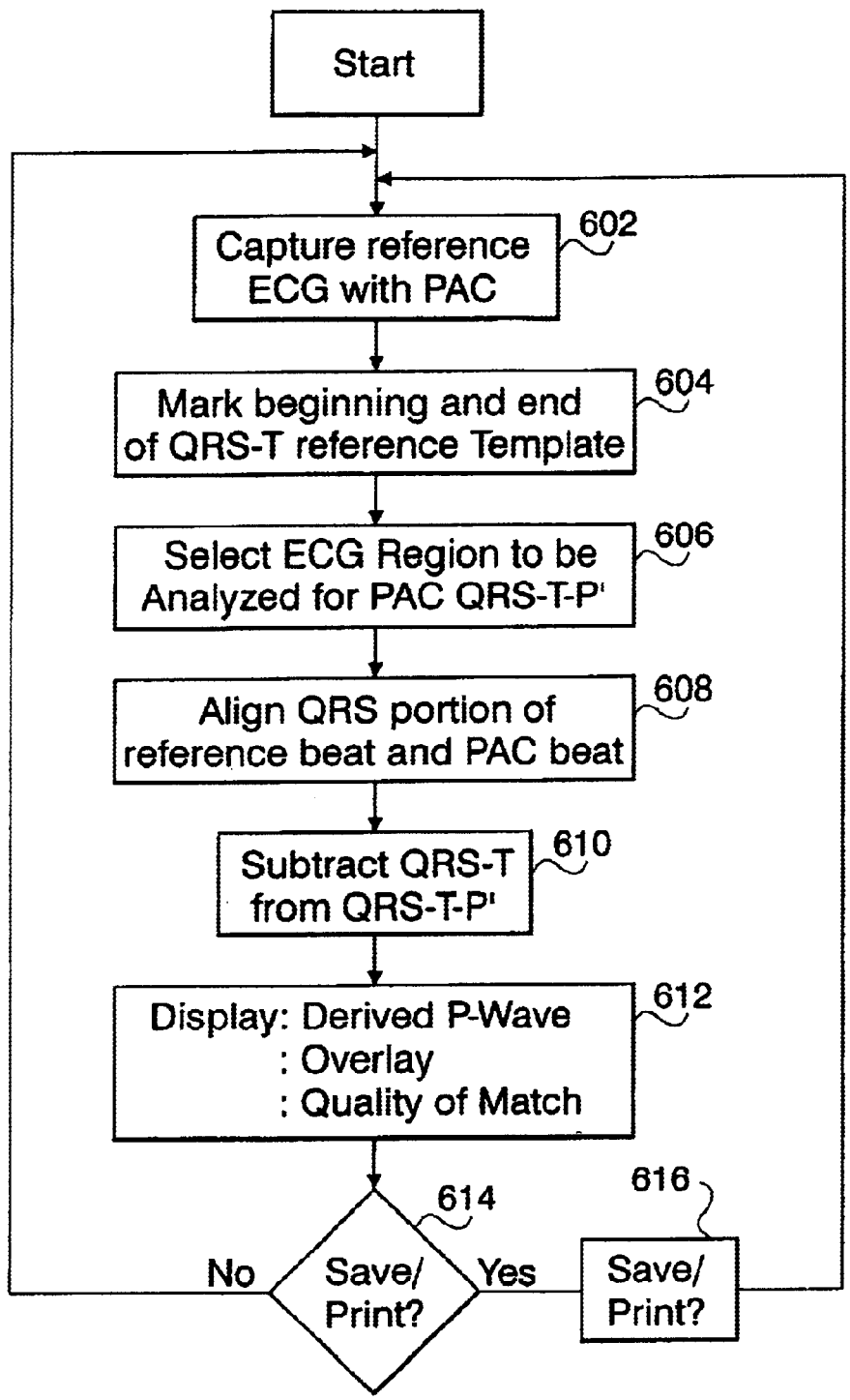
FIG. 6 is a flow diagram showing the process for T-wave Subtraction in accordance with the preferred embodiment.

Referring now to FIG. 6, the operation of the signal processing device 14 of the present invention is described in conjunction with the above structural description of the system 10. As illustrated in FIG. 6, the process begins at step 602 when a clinician captures a PAC and desires to subtract a QRS-T reference template from the PAC. The QRS-T reference template is marked by the clinician at step 604 (as described above) and a region encompassing the PAC is selected by the clinician at step 606 for analysis. The QRS portion of the reference template is aligned for best fit with the QRS complex immediately preceding the PAC at step 608. When the best fit is found, the processor 14 subtracts the QRS-T reference template from the QRS-T-P' segment of the PAC at step 610.

Figure 7:
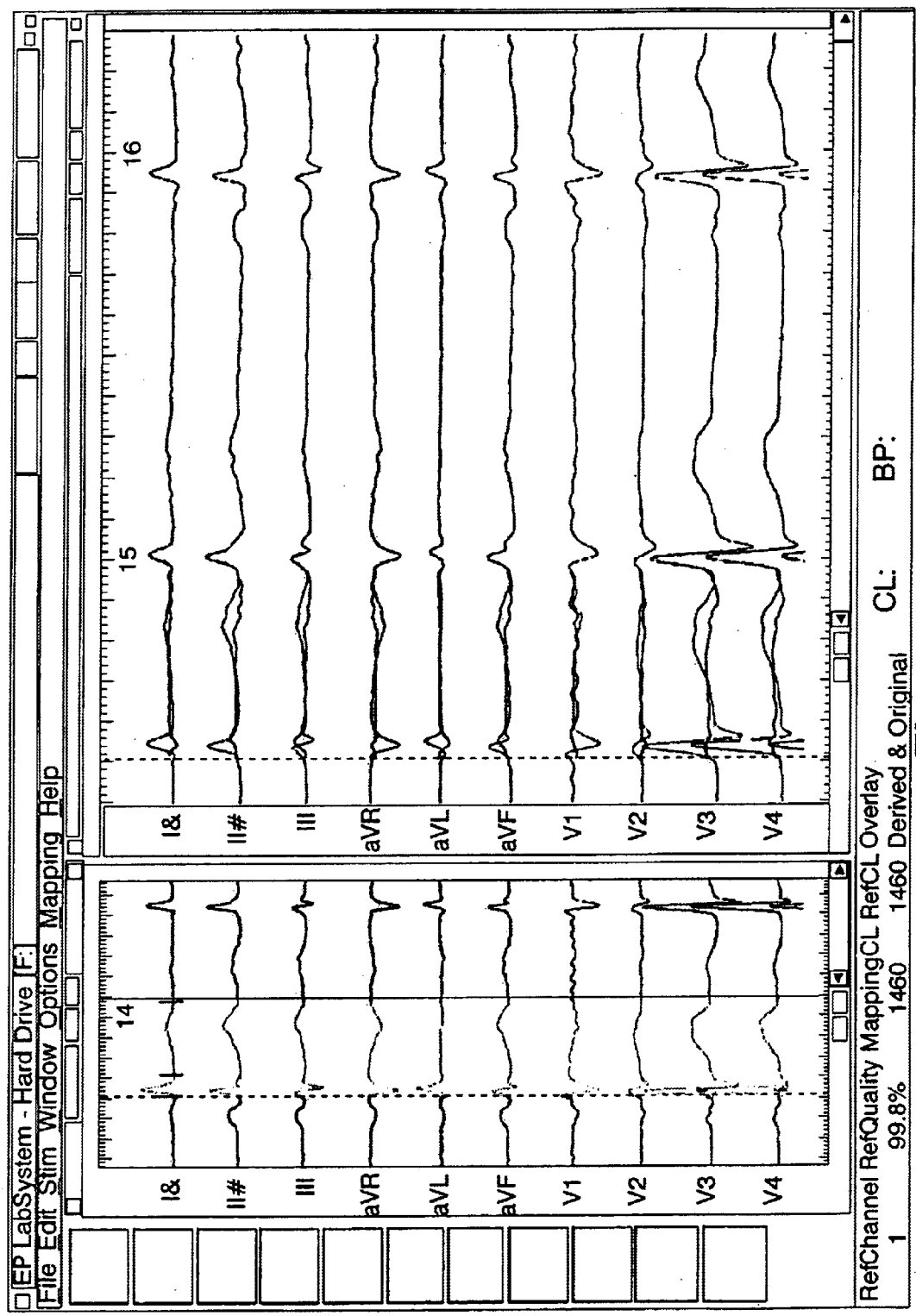
FIG. 7 is a representative computer display interface for T-wave subtraction that can be displayed to an operator.

The difference is the derived P-wave which is output to the display 16 at step 612. This is illustrated in the computer display shown in FIG. 7, in which the leftmost window displays the selected QRS-T reference template between two vertical lines (one dashed line prior to the 14 second mark at the top (highlighted by an arrow), and a second solid line just after the 14 second mark). The rightmost window shows the original PAC waveform with the derived P-wave overlaid on top of the portion of the ECG which occurs in the first 15 seconds. The overlaid and derived P-wave appears as a second graph superimposed over the ECG signals. Visual aids can be provided to automatically align and overlay waveforms for visual comparison on a computer display or a printout.

FIG. 8 illustrates an exemplary display for template matching (without subtraction) that can be displayed to an operator. The leftmost window displays markers which signify the presence and use of the reference template; the reference template beginning at the leftmost vertical line (highlighted by the arrow) and ends at the second vertical line. In this example, the reference template marks the start and finish of a P-wave; however, any waveform segment can be used if the region of interest has been marked for use as a template. The larger display window to the right shows the correlation value for each channel of the 12 Lead ECG as compared to the reference template. The bar graph at the far right is inactive in this example because the analysis region is taken from recorded data rather than real-time data gathered during a medical procedure.

The data can be saved, printed or both, if desired, in response to a user input to do so, as tested at step 614 and implemented at step 616.

From the foregoing, it will be apparent to those skilled in the art that the present invention provides a method for reliably and efficiently recovering a P-wave from a waveform that has overlapping P- and T-waves. Furthermore, the template matching capabilities of the invention provide the added benefit of quickly and objectively comparing ECG waveform components, in their native or derived state. It should also be understood that the correlation, subtraction and derivation methods described herein apply to data that can be acquired from conventional 12 lead surface ECG signals as well as intracardiac signals or combinations of both surface and intracardiac signals.

Two waveforms can have a high correlation to each other but still be poorly matched in absolute terms due to amplitude variation and drift caused by the effects of respiration. This can be a problem when two waveforms are aligned and then subtracted, one from the other. It is for this reason that immediately adjacent beats are usually desirable as the reference (QRS-T) and PAC (QRS-T-P'). This is not always possible and is not practical when performing real time pace mapping.

Figure 3:
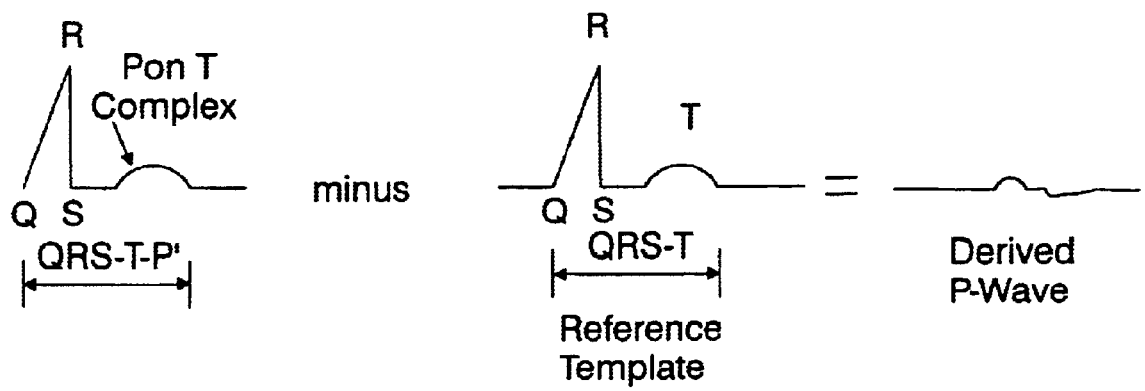
FIG. 3 is a schematic diagram of the T-Wave subtraction.
Figure 9:
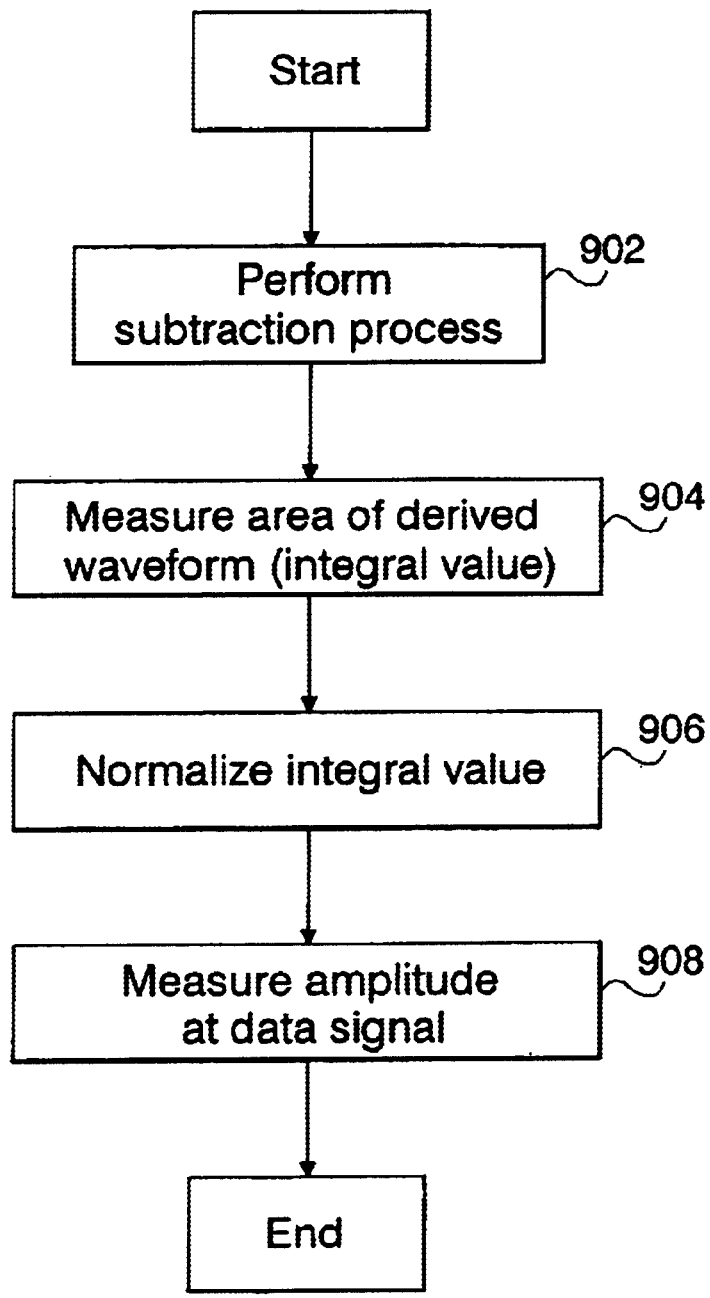
FIG. 9 illustrates a methodology for determining the integrals of a section of the QRS-T segment after the subtraction process.

A methodology for monitoring the quality of the T-Wave subtraction is now described with reference to FIG. 9. At step 902, a subtraction process (as illustrated in FIGS. 3 and 6 and described above) is performed to subtract a QRS-T template from a PAC (QRS-T-P') and thereby derive a waveform. The method of FIG. 9 proceeds by then providing integral calculations that enable a number of measurements of interest to practitioners, including, but not limited to:

measures of QRS residue and the quality of the T-wave subtraction process; measures of the baseline drift, if any; and optimization of the selection of templates to be used in the subtraction process.

At step 904, the area of a derived waveform is measured. At step 906, the integral value is divided by the length of the derived waveform to normalize its value. In addition, at step 908, the amplitude of the normalized integral value is measured and displayed as a voltage at the ECG channel's input. This voltage value is termed the QRS residue.

As described earlier, correlation analysis is used to align the QRS segment of a reference ECG template with the QRS segment of a PAC beat. Thus a further improvement may use the correlation coefficient in conjunction with the so-called QRS residue of the derived waveform to give an indication of the quality if the match between two beats chosen for subtraction. Together, they provide an indicator of the alignment or synchronization quality between the template QRS and the PAC QRS. For a perfect alignment and good subtraction results, the derived QRS segment should be flat indicating a high correlation to the template and the QRS residue should be very small indicating a small difference in absolute amplitudes (including drift).

Compare Display of Paced Signal/Template Matching

Pace-mapping is used to localize the origin of an arrhythmia. Pace-mapping is a time-consuming procedure because electrocardiac signals are sequentially elicited by pacing the heart with an intracardiac electrode and then comparing the elicited signal to a spontaneous arrhythmia signal. The spontaneous arrhythmia signal serves as a template against which the paced signals are matched. A comparison is made between each paced signal and the arrhythmia signal. A close match between the paced signal and the arrhythmia signal is an indication that the origin of the arrhythmia has been identified.

In pace-mapping, the user analyses each iteration to determine whether the most recent paced signal is closer to or further from the origin of the arrhythmia than the second-most recent paced signal or the previous best-matched paced signal. The analysis has conventionally been performed by comparing (or matching) the paced signal to the arrhythmia signal template using either (1) a print-out of the second most recent paced signal or (2) the user's memory of the second-most-recent paced signal. The user decides on the location at which to position the intracardiac electrode for the next paced signal based on this analysis. The user attempts to "walk" the pacing catheter towards the origin of the arrhythmia by sequentially moving the pacing catheter in the direction of paced signal/template matches with comparatively higher correlations and away from paced signal/template matches with comparatively lower correlations. Through this iterative process, the origin of the arrhythmia is eventually identified when a highly correlated match between the paced signal and the template is found.

The compare display method of the present invention shortens the time required to perform pace-mapping by permitting the user to simultaneously view the most recent "step" in the walk (namely, the current probe location) with the just prior step in the walk (namely, the immediately preceding probe location). Using the compare display method of the invention, the user is not required to take the time to print the second-most recent paced signal to inform the next placement or direction for placing the probe. In another embodiment, the user can simultaneously view the most recent "step" in the walk (namely, the current probe location) with the previous best step in the walk (namely, the previous probe location that produced the signal with the best template match).

In one embodiment, the compare display method includes displaying the template in a first panel of a three-way split screen, the most recent paced signal/template match in a second panel of a three-way split screen, and the second-most recent paced signal/template match in a third panel of a three-way split screen.

The pace-mapping procedure of this embodiment can be used to more rapidly locate an ectopic signal due to the simultaneous display of multiple steps in the "walk." A roving catheter is introduced into the heart in a conventional manner. The roving catheter includes a pacing electrode that delivers a signal to depolarize the heart at a location of contact with the heart wall. One or more such electrodes can be included on the roving catheter.

The roving catheter is brought into contact with the heart wall at a first location and a pacing pulse is delivered in a conventional manner. The pacing pulse causes depolarization of the heart and the cardiac waveform elicited by the pacing pulse is obtained.

The pacing electrode of the roving catheter is then energized at a second location on the heart wall, either by energizing a different electrode while maintaining the catheter in place or by moving the catheter to a different location. A second paced signal is elicited at the second location in response to this second energization.

Each of the paced signals is representative of the heart's response to a pacing pulse and comprises at least one heart signal or heart signal segment. A reference template as described previously is used to correlate the heart's response to the signal beat to be located. More particularly, the reference template is a waveform that represents the ectopic signal of interest and the correlation is performed to find the highest coincidence between the reference template and the paced signal. A high correlation (namely, a best fit between the template and the paced signal) is indicative of the roving catheter being disposed on the focus of the ectopic beat.

To better guide the operator during this "walk," the best fit between the reference template and each of the first and second paced signals is simultaneously displayed. As shown in FIG. 8A, a reference template 810 is shown on an electronic display 800 in a central window or frame 820. In another window or frame 830, the reference template 810 is shown in a best-fit overlapping relationship to a first paced signal 840. Additional information can be displayed in the window or frame 830 including a quantitative indicator of the correlation coefficient that was calculated to arrive at the best fit, or a graph indicator of the degree or percentage of the match shown in that window. In yet a further window or frame 850, the reference template 810 is again illustrated, this time in overlapping relationship to a second paced signal 860.

Consequently, the operator can readily review the progress or setbacks in searching for the focus of the ectopic signal.

For simplicity of illustration, FIG. 8A shows a template constructed from only one lead signal and paced signals from only one lead.

Template Matching Using a Trigger and Offset

A trigger and an offset can be set to minimize the computational requirements of processing the template against a data signal and to quickly focus the user on the ROI, thereby resulting in a less time-consuming electrophysiology procedure. The trigger can be any portion of an electrocardiac signal (e.g., a Q-wave, an R-wave), a paced pulse (e.g., the last pulse of a paced stimulation train), an EP waveform event, an activation pattern, or external timing signals (e.g., a stimulator or a QRS detector that provides timing signals such as the last stimulation pulse or the start of a QRS etc.) or any combination of the foregoing. The trigger can be further defined as a property of the designated portion of an electrocardiac signal (e.g., threshold amplitude, peak, slope). For example, the user or a program governing the signal processing functions defines the peak of an R-wave as the trigger, which results in triggering at the point in time when the R-wave has reached a peak. The property of an electrocardiac signal may be either a positive or negative value. For example, either the positive slope or the negative slope of a Q-wave may be defined as the property.

The offset is a time delay that follows the trigger. The offset is typically set in the millisecond range, by the user. A default offset can be stored and used by the governing software. The template matching process is performed following each offset. The offset is preferably defined by the user such that the region of interest appears in the acquired data soon after the expiration of the offset. In this way, computational needs are focused on the region of interest.

Alternatively, the offset can be a negative value representing a desired point in time prior to a triggering event that the operator wishes to use. Thus, the trigger occurs after the beginning of a ROI and the software recalls the data signal from a buffer or storage to commence template matching at a time prior to the triggering event that is equal to the offset value.

Figure 10A:
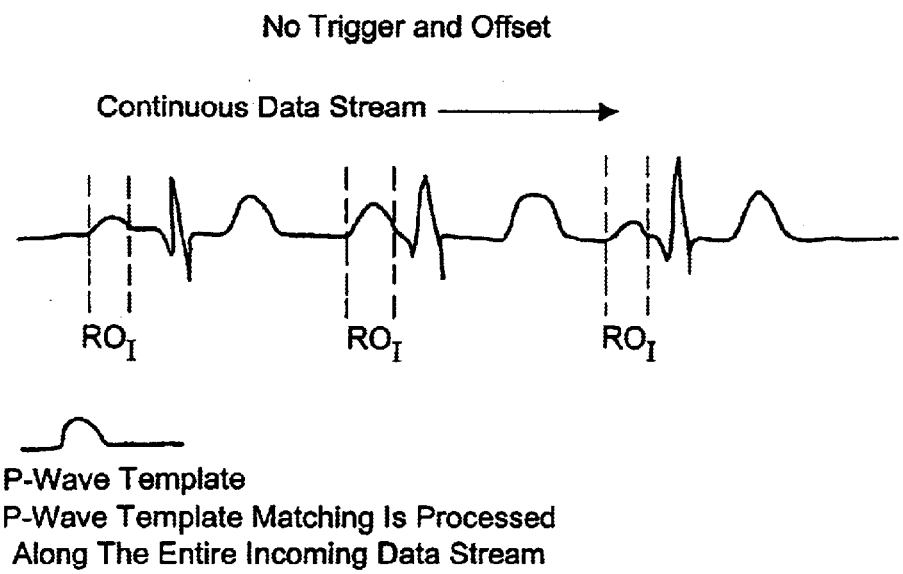

FIG. 10(a) illustrates a process in which template matching is performed without regard to a trigger or an offset. In this mode of operation, the entire incoming stream of data is processed for template matching and the user must observe data both within and outside of the ROI.

Figure 10B:
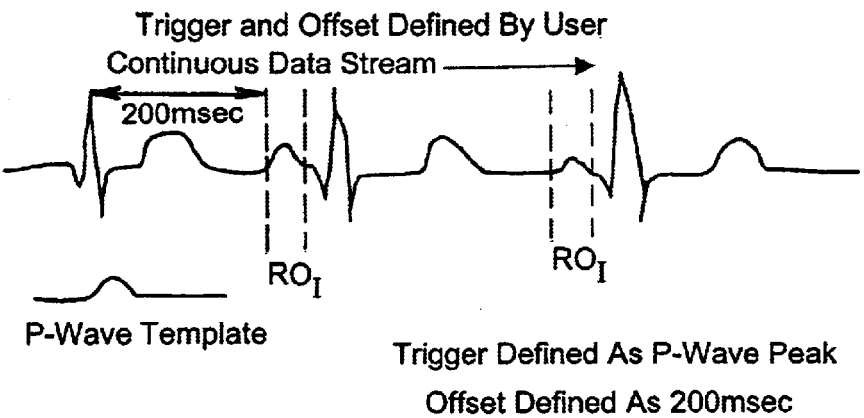

FIG. 10(b) illustrates the advantages of the use of a trigger and offset. A user plans to use the method of template matching on a stream of real-time ECG data. The user's template is an ectopic P-wave. The user selects R-wave peaks as the trigger and 200 milliseconds as the offset. This offset is selected, for example, on the basis of an expectation that P-waves (the ROI) will appear at a certain time following the trigger. Real-time data is then acquired. Rather than processing a continuous stream of incoming data, the microprocessor identifies the trigger event, delays for the time period of the offset, and then begins the template matching computations close in time to the ROI, thereby minimizing template matching processing computational effort. The user can focus on the template match performed in the ROI without the distraction of irrelevant comparisons performed outside of the ROI.

Figure 10C:
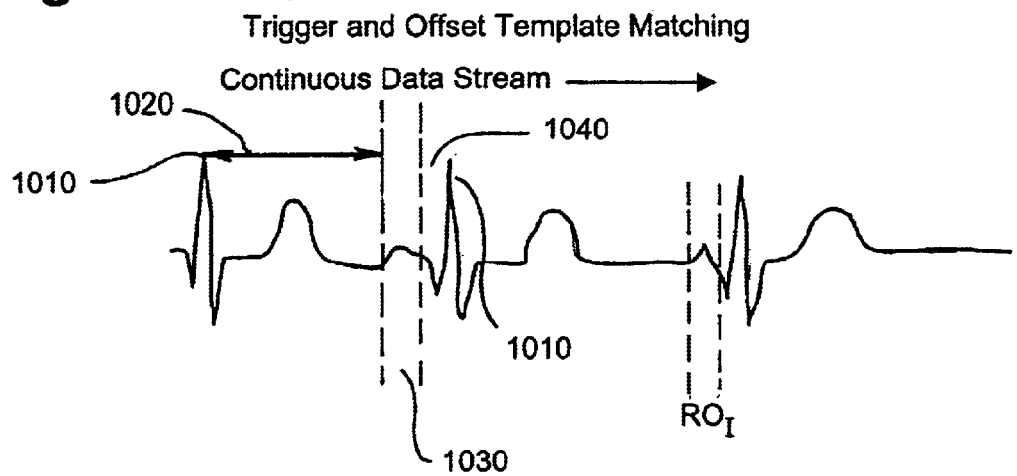

Thus, with reference to FIG. 10(c), the trigger is identified at the peak of the R-wave as indicated by arrow 1010. That trigger point begins the offset interval 1020, which in this example is a 200 ms. During that 20 ms interval, portions of the cardiac signal that precede the region of interest are not processed, such as the bounce off of the R-wave and the S-wave. Thereafter, the ROI 1030 occurs and this portion of the cardiac cycle is matched against the template, as previously described.

Optionally, the user can select a termination of the matching interval 1030. For example, the termination of the matching interval 1030 can coincide with a cardiac event such as detection of a Q-wave or some other waveform segment, or with a cardiac parameter such as threshold amplitude or slope, or it can be a prescribed time after the offset, or can be a parameter relating to the correlation computation such as exceeding a correlation coefficient threshold. In any such designated event, there is a window of time 1040 prior to the next trigger 1010 during which the data signals need not be processed. This cycle proceeds again at the next trigger 1010. Consequently, the foregoing method in which a trigger and offset are utilized minimizes template matching processing outside of the ROI and permits the user to focus on template matches within the ROI without the delay and distraction brought on by sifting through the irrelevant template matches outside of the ROI.

Multiple Spontaneous Arrhythmia Matching and Pace Mapping

It can be difficult for a user to discern whether one or more than one arrhythmia is present. For example, two close in space, but separate and distinct, ectopic foci can emit arrhythmia signals that are morphologically similar. Determining the number of distinct arrhythmias and the location of the each arrhythmia's ectopic focus are diagnostically and therapeutically significant steps for subsequent treatment of the arrhythmias by ablation of each arrhythmia's ectopic focus. In accordance with the following methods, a user can (1) determine the number of distinct arrhythmias present and (2) locate the ectopic focus of each distinct arrhythmia using pace mapping.

(1) Determining the Number of Distinct Arrhythmias

A first arrhythmia signal is acquired and defined by the user as a template (template 1). A second arrhythmia signal is acquired and selected for correlation to template 1. A correlation coefficient is calculated to find the best alignment between template 1 and the second arrhythmia signal. A best alignment correlation that falls below prescribed criteria (e.g., a minimum correlation coefficient) indicates that the first arrhythmia signal and the second arrhythmia signal originate from different ectopic foci because the distinct ectopic foci cause distinct arrhythmic signal patterns. A best alignment correlation that meets or exceeds the prescribed criteria indicates that the first arrhythmia signal and the second arrhythmia signal are the same signal and, thus, originate from the same ectopic focus.

The method described herein of determining the number of distinct arrhythmias can be repeated to permit determination of a plurality of distinct arrhythmias. For example, a user suspects that three distinct arrhythmias may be present. Following the correlation between template 1 and the second arrhythmia signal (as described above), the user determines that the first arrhythmia signal and the second arrhythmia signal represent distinct arrhythmias because the correlation fell below the correlation criteria prescribed by the user. The user defines the second arrhythmia signal as template 2. The third arrhythmia signal is acquired. The third arrhythmia signal is selected for correlation to template 1 and template 2, in sequence. A correlation between the third arrhythmia signal and any one of template 1 or template 2 that meets or exceeds the prescribed criteria indicates that a total of two ectopic foci are present. If the sequential correlations between the third arrhythmia signal and templates 1 and 2 fall below the prescribed criteria then three ectopic foci are present. The method of determining the number of distinct arrhythmias can be repeated until all arrhythmia signals are accounted for and the total number of distinct arrhythmia signals has been determined. Each distinct arrhythmia signal can define a distinct template.

(2) Locating the Ectopic Focus of Each Distinct Arrhythmia Using Pace Mapping

The methods according to the invention facilitate pace mapping of a plurality of ectopic foci resulting in a less time-consuming mapping procedure. Following the elicitation of a paced signal by a pace mapping catheter, the user can sequentially correlate the paced signal to each of a plurality of templates. Each of the plurality of templates represents a distinct arrhythmia signal as defined by the user. A correlation between a paced signal and one of the plurality of templates that meets or exceeds prescribed criteria (e.g., a minimum correlation coefficient) indicates that the location in the heart that was stimulated by the pace mapping catheter (and that resulted in the paced signal) is the ectopic focus of the distinct arrhythmia signal that defines the template used in the correlation. The user can then ablate that focus. The user maneuvers the pace mapping catheter in the heart and elicits paced signals for subsequent sequential template correlations until all ectopic foci (as represented by the plurality of templates) have been identified and/or ablated.

Activation Pattern Matching

While the reference templates in the foregoing discussion comprised a defined interval of time of a cardiac signal acquired from one or more leads, the invention is not so limited. As understood by those in the art, a reference template can be defined across different times, as now discussed in connection with FIG. 11. As shown in FIG. 11, a user can define one template that includes electrocardiac signals from different leads, with such signals occurring at different times. Preferably, the reference ECG signal is captured using a standard 12 lead device and/or one or more intracardiac leads. In FIG. 11, the user has selected signals from ECG surface leads I, II, and III and intracardiac leads 1, 2, and 3 for the template. The user has marked a begin point (A) and an end point (B) of the ECG lead I waveform, a begin point (C) and an end point (D) of the ECG lead II waveform, a begin point (E) and an endpoint (F) of ECG lead III, a begin point (G) and an end point (H) of intracardiac lead 1, a begin point (I) and an end point (J) of intracardiac lead 2, and a begin point (K) and an end point (L) of intracardiac lead 3. Thus the user has defined a template constructed of signals that appear on different leads, with some signals having begin points that occur at the same time (A, C, E) and end points that occur at the same time (B, D, F) as described previously, while others have begin points that occur at different times (e.g., E, G, I, K) and end points that occur at different times (e.g., F, H, J, L). Template matching then proceeds as described in connection with steps 506, 508, 510, 512, 514, and 516. Such a template can also be used for template subtraction as described in connection with the steps of FIG. 6.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A method for locating an ectopic beat during pace-mapping with a roving catheter, comprising the steps of:
    (a) eliciting at least first and second paced signals from respective first and second locations of the roving catheter;
    (b) using a correlation coefficient calculation on the elicited first and second paced signals to identify a best fit between a reference template and each of the first and second paced signals; and
    (c) simultaneously displaying on a display the best fit for each of the first and second paced signals.

2. The method of claim 1, whereas the reference template comprises a waveform segment of a single heart signal which includes an arrhythmic component.

3. The method of claim 2, further comprising the step of displaying the reference template on the display while the first and second paced signals are being displayed.

4. The method of claim 1, including the additional step of displaying a quantitative indicator of each correlation coefficient calculation on the display.

5. The method of claim 1, wherein the data is acquired from multiple leads and wherein the quantitative indicator is a composite average of coefficients calculated from the multiple leads.

6. The method of claim 1, wherein the quantitative indicator is displayed as a graph showing percentage of fit.

7. The method of claim 1, wherein the first paced signal is the most recent paced signal and the second paced signal is the paced signal prior to the first paced signal having the best fit.

8. A method for tracking ectopic beats through template matching, comprising the steps of:
    (a) establishing a reference template over an interval of a first ECG signal;
    (b) monitoring a data signal for a triggering event;
    (c) initiating an offset period in response to the triggering event; and
    (d) after the offset period has elapsed, using a correlation coefficient calculation on the data signal to identify a best fit between the reference template and the data signal over the interval.

9. The method of claim 8, wherein the triggering event is defined by the user.

10. The method of claim 8, wherein the triggering event comprises one of: a waveform property, a pacing pulse, an activation sequence, an external timing signal, and a combination thereof.

11. The method of claim 8 wherein the data signal is acquired from a real-time data stream which includes successive triggering events, the method including the additional step of repeating steps (c) and (d) in response to each successive triggering event in the real-time data stream.

12. The method of claim 8 wherein the correlation coefficient calculation terminates upon a designated event.

13. The method of claim 12 wherein the designated event is a correlation coefficient value threshold.

14. The method of claim 8, including the additional step of processing a portion of the data signal corresponding to the identified best fit.

15. The method of claim 14, wherein the processing step comprises subtracting the reference template from the portion of the data signal corresponding to the identified best fit to define a derived waveform, the method including the additional step of displaying the derived waveform on a display.

16. The method of claim 14, wherein the processing step comprises ablating heart tissue.

17. A method for identifying multiple distinct arrhythmias comprising the steps of:
    (a) acquiring a first arrhythmia signal within a sinus rhythm;
    (b) defining the first arrhythmia signal as a first template;
    (c) acquiring a second arrhythmia signal;

(d) correlating the first template and the second arrhythmia signal;

(e) identifying the second arrhythmia signal as a second, distinct arrhythmia if the correlation fails prescribed criteria.

18. A method for identifying multiple distinct arrhythmias comprising the steps of:

(a) acquiring a first arrhythmia signal;

(b) defining the first arrhythmia signal as a first template;

(c) acquiring a second arrhythmia signal;

(d) correlating the first template and the second arrhythmia signal;

(e) identifying the second arrhythmia signal as a second, distinct arrhythmia if the correlation fails prescribed criteria wherein greater than two arrhythmia signals are present, and comprise a set of templates, the method further comprising the steps of:

(f) defining the second, distinct arrhythmia as a second template;

(g) acquiring an additional arrhythmia signal;

(h) sequentially correlating the additional arrhythmia signal to each template in the set of templates;

(i) identifying the additional arrhythmia signal as a distinct arrhythmia signal if the correlation fails prescribed criteria;

(j) defining the additional distinct arrhythmia signal as an additional template and repeating steps (f)–(j) until no additional arrhythmia signals remain that fail the prescribed criteria.

19. The method of claim 18, including the additional steps of:

(a) acquiring a paced signal produced by apace mapping catheter in or adjacent to the heart;

(b) correlating the paced signal sequentially to each of the templates in the set;

(c) identifying the location of an ectopic focus when a correlation of the paced signal to one of the templates meets or exceeds prescribed criteria.

20. The method of claim 19, further comprising the step of abating the ectopic focus.

21. The method of claim 19, further comprising repeating steps (a)–(c) until the ectopic focus location of each distinct arrhythmia signal has been identified.

22. A method for deriving a p-wave signal from a premature atrial contraction ("PAC") beat to assist a person in diagnosing a heart, comprising the steps of:

(a) selecting a QRS-T segment of a reference ECG signal;

(b) permitting a user to mark a begin a point and an end point of the selected segment of the reference ECG signal;

(c) defining a reference template as being a waveform segment between the marked begin and end points of the selected segment of the reference ECG signal;

(d) acquiring the PAC beat at the signal processing unit from multiple leads;

(e) processing the PAC beat so as to derive the p-wave signal, wherein the derived p-wave is a derived, spontaneous p-wave template;

(f) maneuvering a pace mapping catheter within or adjacent the atria while pacing the heart while repeating the acquiring and processing steps so as to derive a paced p-wave; and (g) comparing the derived, paced p-wave to the derived, spontaneous p-wave using a correlation coefficient to identify a best fit between the derived, spontaneous p-wave template and the derived, paced p-wave.

23. The method of claim 22, wherein the ECG signal is captured by a lead.

24. The method of claim 23, wherein the lead is an intracardiac lead.

25. A method for determining a most likely site of origin of a spontaneous P-wave comprising:

(a) defining a spontaneous P-wave as a template;

(b) maneuvering a pace mapping catheter within or adjacent the atria (c) pacing at a location in or adjacent the atria using a pace-mapping catheter;

(d) acquiring a paced P-wave signal from the pace-mapping catheter;

(e) comparing the spontaneous P-wave template to the paced P-wave signal; and (f) repeating steps (b), (c), (d), and (e) until such time that the spontaneous P-wave template and the paced P-wave signal correlate with one another within a prescribed criterion.

26. The method according to claim 25, wherein the paced P-wave signal is superimposed on an electrocardiac signal, the method further comprising the steps of:

(a) selecting a QRS-T segment of a reference ECG signal;

(b) permitting a user to mark a begin point and an end point of the selected segment of the of the selected segment of the reference ECG signal;

(c) defining a reference template as being a waveform segment between the marked begin and end points of the selected segment of the reference ECG signal;

(d) subtracting the reference templates from the electrocardiac signal having the superimposed paced P-wave signal to define a resultant derived, paced P-wave signal; and (e) comparing the resultant derived, paced P-wave signal to the spontaneous P-wave template.

27. The method of claim 25 wherein the spontaneous P-wave is a spontaneous, derived P-wave.

28. A method for tracking ectopic beats through template matching, comprising the steps of:

(a) capturing a first ECG signal in a signal processing unit;

(b) permitting a user to mark a begin point and an end point of the captured first ECG signal;

(c) defining a reference template as being a waveform segment between the marked begin and end points of the first ECG signal;

(d) acquiring data at the signal processing unit; and (e) using a correlation coefficient calculation on the acquired data to identify a best fit between the reference template and the acquired data;

wherein the defining step comprises defining the reference template as a set of waveform segments that are obtained from a plurality of electrocardiac leads between marked begin and end points.

29. The method of claim 28, wherein the begin points of the waveform segments occur at different points in time.

30. The method of claim 28, wherein the end points of the waveform segments occur at different points in time.

* * * * *